Figure 1:
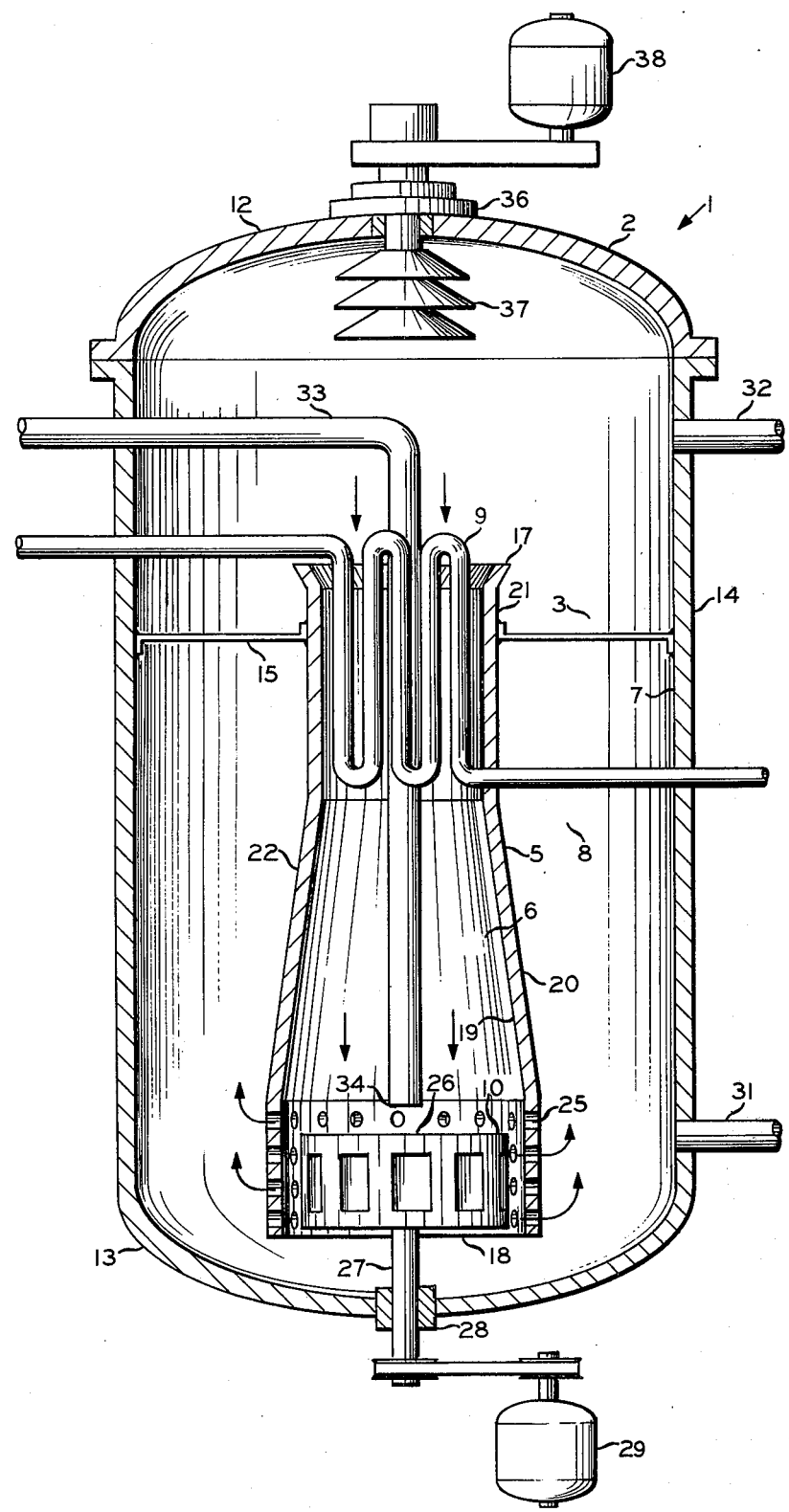

United States Patent [19]

Malick

[11] 3,977,946

[45] Aug. 31, 1976

[54] FERMENTATION APPARATUS

[75] Inventor: Emil A. Malick, Bartlesville, Okla.

[73] Assignee: Phillips Petroleum Company, Bartlesville, Okla.

[22] Filed: Jan. 24, 1975

[21] Appl. No.: 543,793

[52] U.S. Cl. .............................. 195/142; 195/143
[51] Int. Cl.[2] .......................................... C12B 1/16
[58] Field of Search ............................ 195/142, 143

[56] References Cited
UNITED STATES PATENTS

| | | | |
|---|---|---|---|
| 2,111,726 | 3/1938 | Plews .................................. | 195/143 |
| 2,244,902 | 6/1941 | Stich ................................... | 195/142 |
| 2,522,947 | 9/1950 | Hatch et al. ........................ | 195/143 |
| 2,530,814 | 11/1950 | Becze et al. ........................ | 195/143 |
| 2,750,328 | 6/1956 | Stimpson et al. .................. | 195/142 |
| 2,983,652 | 5/1961 | Baerfuss ............................. | 195/143 |
| 3,625,834 | 12/1971 | Muller ................................. | 195/142 |

*Primary Examiner*—Alvin E. Tanenholtz

[57] ABSTRACT

An apparatus for culturing a microorganism by an aerobic fermentation process. The apparatus includes a vessel having a generally centrally located draft tube mounted in a chamber defined by the vessel with the draft tube forming a flow path. The vessel and draft tube are shaped such that the flow path diverges in the direction of ferment flow therethrough. The draft tube has opposite ends with a pump positioned adjacent one end to induce circulation of ferment through the draft tube and along the flow path. A heat exchanger is suitably mounted in the vessel and is in heat transfer relation with the ferment so as to maintain a predetermined operating temperature.

5 Claims, 1 Drawing Figure

FERMENTATION APPARATUS

In recent years there has been increasing concern about the supply of protein for direct or indirect consumption by people. This is of particular importance in countries which do not have large sources of agricultural products to supply the protein necessary for good nutrition. One hope to alleviate this situation has been the production of protein from microorganisms which would be a major supply of protein independent of agricultural land use. Production of protein by this method is important because it does not depend upon agricultural or climatic conditions, it provides rapid cell growth rates and cell growth is not dependent upon surface or sunlight conditions.

One particularly effective method of growing single cell protein is by aerobic fermentation. By this process, a suitable microorganism is selected from bacteria, yeasts or molds and is grown on a suitable substrate or feedstock which supplies carbon and energy for growth. Preferably, the feedstock includes dissolved oxygen or is in the presence of oxygen in the fermenter and can also contain other elements or substances such as mineral nutrients which are required for growth of the microorganism. Such mineral nutrients usually provide a source of phosphate, magnesium, calcium, sodium, manganese, molybdenum and copper ions. Generally, the fermentation process requires a source of assimilable nitrogen which may be furnished by such things as ammonium salts, ammonium hydroxide, anhydrous ammonia, urea and the like. In aerobic fermentation processes, relatively large amounts of oxygen are required for the culturing of the microorganisms to produce single cell protein. This can be accomplished by continuously introducing oxygen such as in the form of air into the fermentation vessel. After a suitable concentration of microbial cells has been attained in the fermenter, at least a portion thereof is discharged as fermenter effluent to cell recovery steps. These typically involve centrifuging or otherwise separating the cells from the aqueous medium, washing and drying the cells to provide a cellular product which may be fed directly in some cases to animals such as cattle or may be further treated and refined to recover other forms of protein for consumption by humans as well as animals.

The present invention is adapted for use in aerobic fermentation processes and provides suitable oxygen transfer rates for rapid growth of microorganisms and will provide for efficient dissipation of heat produced by the fermentation process.

The principal objects of the present invention are: to provide a fermenting apparatus which will effect high oxygen transfer rates for improved microorganism growth; to provide such an apparatus which will effect high velocity flow of ferment by a heat exchanger for improved heat transfer; to provide such an apparatus which will permit expansion of ferment as same flows along a flow path; to provide such an apparatus which will provide good mixing and circulation of the ferment; and to provide such an apparatus which is well adapted for its intended use, economical manufacture and easy to maintain.

Other objects and advantages of the present invention will become apparent from the following description taken in connection with the accompanying drawings wherein are set forth by way of illustration and example certain embodiments of the present invention.

FIG. 1 is a side-elevational section view of a fermenting apparatus.

Referring more in detail to the drawing:

As required, detailed embodiments of the present invention are disclosed herein, however, it is to be understood that the disclosed embodiments are merely exemplary of the invention which may be embodied in various forms. Therefore, specific structural and functional details disclosed herein are not to be interpreted as limiting, but merely as a basis for the claims and as a representative basis for teaching one skilled in the art to variously employ the present invention in virtually any appropriate detailed structure.

The reference numeral 1 designates generally a fermentation apparatus which includes a vessel 2 which has a chamber or reaction zone 3 therein. A draft tube 5 is mounted in the reaction zone 3 and has a hollow interior 6 which forms a flow path. The draft tube 5 is spaced from an interior surface of the vessel 2 forming a flow path 8 therebetween. Heat exchange means 9 are in heat transfer relation with the reaction zone 3 and are operable to effect transfer of heat with ferment contained in the reaction zone 3. Circulation inducing means 10 are also provided to positively induce circulation of ferment through the flow defined by the draft tube 5 and flow path 8.

Any suitable vessel 2 can be used and, as shown, the vessel has top and bottom walls 12 and 13, respectively, and can have a generally cylindrically shaped side wall 14. Preferably, the vessel 2 is made of a durable and rigid material such as stainless steel which is easy to clean and maintain in a sanitary condition. The draft tube 5 is suitably mounted in the reaction zone 3 as by brackets 15 and preferably is centrally located therein. The draft tube 5 has an upper end 17 which is open and also has a bottom end 18. An interior surface 19 is contoured or shaped in such a manner as to provide a diverging flow path from the open end 17 to the bottom end 18 for a purpose to be later described. In a preferred form of the present invention, an exterior draft tube surface 20 is shaped or contoured in relation to the interior surface 7 of the vessel 2 to define the flow path 8 which preferably diverges in the direction of flow of ferment therethrough. As shown, the upper disposed end 17 of the draft tube can be flared or bell-shaped with the draft tube then having a generally straight cylindrical portion 21 which continues on into a truncated cone-shaped portion 22. However, it is to be noted that other shapes or configurations of draft tube can be provided to effect the diverging flow path in the direction of flow.

The circulation inducing means 10 can be of any suitable type such as a centrifugal impeller or turbine preferably positioned adjacent to the bottom end 18 and operable to induce circulation of ferment from the end 17 to the end 18 through a flow opening and into the flow path 8. As shown, the draft tube 5 has a plurality of openings 25 which provide the flow openings or outlets for ferment circulated by the means 10. The circulation inducing means 10, as illustrated, includes a pump portion 26 mounted on a shaft 27 which is rotatably mounted in a bearing arrangement 28 and the shaft is in driving engagement with a suitable power source such as an electric motor 29.

Means 31 are provided for supply of feedstock to the reaction zone 3 with the feedstock typically comprising a source of carbon and energy such as methanol and mineral nutrients necessary for the growth of microorganisms. Means 32 are also provided which are operable for the removal of product produced in the reaction zone. Any suitable means 31 and 32 can be used as is known in the art and positioned at any desired location on the fermenter as will best serve the particular process. Also, because fermentation processes are typically of an aerobic type, oxygen is supplied to the reaction zone 3 by means 33 which can be of any suitable type. It is to be understood that the term "oxygen" can include any form of oxygen either alone, or in combination with other substances such as air or osygen-enriched air. Preferably, the means 33 include a conduit which extends into the reaction zone 3 and has an open end 34 positioned adjacent the circulation inducing means 10 so that oxygen is dispersed within the ferment.

Because fermentation processes are generally of an exothermic nature, heat must be removed to maintain the process at the desired operating temperature. The heat exchange means 9 accomplishes this and can be of any suitable type and preferably is positioned within the draft tube 5 and restricts flow of ferment therethrough by constricting the open end 17 of the draft tube 5. It has been found that to achieve high oxygen transfer rates certain fermentation processes are advantageously carried out as a foam-type process although the present apparatus is not limited thereto. If a foam process is used, it is desirable to provide foam breaking means 36 which is operable to separate the foam into a liquid phase and a gas phase wherein the gas phase can be exhausted from the reaction zone 3. Normally the gas phase is a gas of reduced oxygen content as oxygen is used in the fermentation process. Any suitable foam-breaking means can be provided and can include either singularly or in combination a mechanical foam-breaker or a chemical defoaming agent. In the illustrated structure the foam-breaking means 36 includes centrifugal foam-breaking discs 37 which are in driving engagement with a power source such as an electric motor 38.

The present invention is more fully understood by a description of the operation thereof. After the fermentation apparatus has been sterilized and prepared for the conducting of a fermentation process therein, a suitable feedstock is introduced into the reaction zone 3 by the feedstock feed means 31. A suitable microorganism is then introduced into the reaction zone 3 so that the microorganism can be cultured for the production of a product such as single cell protein. Illustrative microorganisms useful for this purpose would be yeasts, such as *Hansenula polymorpha* or bacteria *Pseudomonas methanica*. After an adequate amount of feedstock is introduced into the reaction zone 3 the circulation inducing means 10 effects circulation of the ferment upwardly through the flow path 8 and downwardly through the draft tube 5. Product produced by the culturing of the microorganism is withdrawn from the reaction zone 3 by the product removal means 32 whereby same is then conducted to processing equipment as is known in the art for further processing of the product. As the ferment flows past the heat exchanger 9, heat is removed to maintain the desired operating temperature. During flow of the ferment through the draft tube 5 because of the diverging contour of the interior of the draft tube 5, it allows for expansion of the ferment, if the ferment is not entirely liquid, whereby the ferment is cooled further. As the ferment is discharged through the openings 25 and into the flow path 8, flow along the diverging flow path allows further cooling of the ferment due to expansion, if same is not entirely liquid, thereof. Preferably, the cross-sectional area of the flow path 8 adjacent the opening 25 is equal to or greater than the cross-sectional area of the draft tube 5 adjacent the circulation inducing means 10. However, it is to be noted that other ratios of areas can be provided as is required for optimization of the fermentation process. It is to be further noted that the interior surface 7 can be contoured relative to the exterior draft tube surface 20 so as to provide different shapes of flow paths 8 so long as it diverges in the direction of flow of ferment therethrough.

It is to be understood that while I have illustrated and described certain forms of my invention, it is not to be limited to the specific form or arrangement of parts herein described and shown.

What is claimed and desired to be secured by Letters Patent is:

1. A fermentation apparatus comprising:
   a. a vessel having a chamber therein adapted to contain a fluid and having a wall partially defining said chamber, said vessel having first and second ends;
   b. a draft tube mounted in said chamber between said first and second ends and is spaced from said vessel wall forming a first flow path therebetween, said draft tube has a second flow path therethrough and has a generally cylindrical first portion adjacent an upstream end and has a downstream diverging portion which continues on downstream from the first cylindrical portion, said draft tube having a second cylindrical portion continuing downstream from said diverging portion, said second cylindrical portion having a plurality of through aperatures communicating between said first and second flow paths;
   c. heat exchange means mounted in said chamber in a portion of the second flow path formed by the first cylindrical portion;
   d. pump means mounted in said chamber and operable for effecting circulation of a fluid in said chamber, said pump means has a pump portion positioned between the second end and a position immediately adjacent the downstream end of said diverging portion with said diverging portion terminating at a position upstream of said pump portion, said pump portion is remote from an upstream end of the diverging portion whereby said second flow path diverges downstream from a position upstream of said pump portion.

2. The apparatus as set forth in claim 1 including:
   a. means communicating with said chamber and operable for introducing oxygen into said chamber.

3. The apparatus as set forth in claim 2 including:
   a. means communicating with said chamber and operable for continuously introducing feedstock into said chamber; and
   b. means communicating with said chamber and operable for continuously removing product from said chamber.

4. The apparatus as set forth in claim 3 including:
   a. foam-breaking means positioned in said chamber and operable for breaking a foam into a liquid phase and a gas phase.

5. The apparatus as set forth in claim 3 wherein:
   a. said draft tube having an exterior surface shaped such that said first flow path diverges in the direction of flow therethrough.

* * * * *